(12) United States Patent
Hsiung et al.

(10) Patent No.: US 7,794,778 B2
(45) Date of Patent: Sep. 14, 2010

(54) AMPEROMETRIC SENSOR FOR URIC ACID AND METHOD FOR THE SAME

(75) Inventors: Shen-Kan Hsiung, Jungli (TW);
Jung-Chuan Chou, Douliou (TW);
Tai-Ping Sun, Jhongli (TW); Mei-Ling Cheng, Taoyuan (TW)

(73) Assignee: Chung Yuan Christian University, Taoyuan County (TW)

( * ) Notice: Subject to any disclaimer, the term of this patent is extended or adjusted under 35 U.S.C. 154(b) by 1343 days.

(21) Appl. No.: 11/211,679

(22) Filed: Aug. 26, 2005

(65) Prior Publication Data

US 2007/0240983 A1    Oct. 18, 2007

(51) Int. Cl.
*G01N 1/31* (2006.01)
*B05D 3/00* (2006.01)
*C25B 11/12* (2006.01)
*H01L 21/00* (2006.01)

(52) U.S. Cl. .................. 427/2.13; 427/58; 204/403.03; 204/403.01

(58) Field of Classification Search ................ 204/403.01–403.15; 435/174, 288, 817; 427/2.13, 427/58; 438/48
See application file for complete search history.

(56) References Cited

U.S. PATENT DOCUMENTS 4,927,516 A * 5/1990 Yamaguchi et al. ...... 204/403.1

5,185,256 A * 2/1993 Nankai et al. ............... 435/174
2005/0067280 A1* 3/2005 Reid et al. ............. 204/403.14

OTHER PUBLICATIONS

"Technical Data Sheet AMICON C 850-6." Data Sheet Catalog. Emerson & Cuming: a National Starch and Chemical Company. Web. Sep. 11, 2009. <http://www.datasheetcatalog.org/datasheets2/76/76026_1.pdf>.*
Barmin, Anatoli V., Arkadi V. Eremenko, Ilya N. Kurochkin, and Andrei A. Sokolovsky. "Cyclic Voltammetry of Ferrocenecarboxylic Acid Monomolecular Films and their Reaction with Glucose Oxidase." Electroanalysis 6 (1994): 107-12.*

* cited by examiner

*Primary Examiner*—Nam X Nguyen
*Assistant Examiner*—Kourtney R Salzman
(74) *Attorney, Agent, or Firm*—Rosenberg, Klein & Lee

(57) ABSTRACT

An amperometric sensor for uric acid and a manufacturing method thereof are disclosed, in which polyacrylamide is used to fix catalase, uricase and ferrocenecarboxylic acid on a working electrode. In determining concentration of uric acid, hydrogen peroxide is produced when enzyme and uric acid react with each other and then a reduction current generated from enzyme on the electrode with an external voltage 200 mV applied is detected. In determining concentration of uric acid, a concentration range of 2.5-20 mg/dl is achieved and sensibility of the sensor in a linear portion is 5.17 uAcm$^{-2}$(mg/dl)$^{-1}$. In addition, reaction time required for the reaction between enzyme and uric acid is 5.17 uAcm$^{-2}$(mg/dl)$^{-1}$.

8 Claims, 4 Drawing Sheets

AMPEROMETRIC SENSOR FOR URIC ACID AND METHOD FOR THE SAME

BACKGROUND OF THE INVENTION

1. Field of the Invention

The present invention relates to an amperometric sensor for uric acid and a manufacturing method therefor. More particularly, the present invention relates to a disposable amperometric sensor for uric acid suitable for various biosensing uses and a method therefor in which a carbon electrode is fabricated by a stencil printing process, contributing to mass production of such sensor.

2. Description of the Prior Art

There are some quantitative analysis technologies set forth for organic matters in the past. Such prior art may be, for example, an article by Jian-yuan, Chen, 1993, entitled "Development and application of biosensors", Bioindustry, vol. 4, issue 3, pp. 205-212; an article by Ding-Guo, Huang, Wu-shun and Rui-qi, Zheng, 1996, entitled "Introduction to biosensors and future development therefor", Bioindustry, vol. 7, issue 4, pp. 291-298; an article by S. Zhang, G. Wright and Y. Yang, 2000, entitled "Materials and techniques for electrochemical biosensor design and construction", Biosensors and Bioelectronics 15: 273-282. However, disadvantages have been seen in practical uses with respect to these technologies. For example, complex operating processes, prolonged analysis time and pricy equipment are involved with such quantitative analyses. Further, such analysis technologies may not be applied for detection of continuous processes. Therefore, a solution capable of compensating for the disadvantages of the conventional quantitative analyses has been sought. A biosensor, which is achieved by combination of biochemistry, electronic circuits, material science, optics, among others, can be such solution and may be used in a wide range of fields.

The following will be made to introduction to development of the biosensors for the recent 30 years. The biosensors were commenced from the concept of an enzyme electrode set forth by Clark and Lycons, 1962, in which glucose oxides and an oxygen-containing electrode are combined to determine a consumed amount of the oxygen in a reaction process so as to determine concentration of the glucose. In 1967, Updike and Hicks fixed glucose oxide in polyacylamide gel to determine concentration of the glucose with the presence of the oxygen-containing electrode. Based on this principle, a current-determination based enzyme electrode was manufactured as a first generation biosensor.

As of 1975, Yellow Springs Instruments (YSI) of the United State began to render such technology into production. In 1979, a first generation sensor product, glucose determining pen, hit the market (Cass, 1989), which was used in medical examinations. For recent years, biosensors have been greatly improved with the aid of mature development of biochemistry, electrochemistry, material science and the like, and are anticipated to find more applications and values.

Currently, colorimetric and electrochemical methods are typically used for uric acid detection. The colorimetric method comprises a reducing method and a spectrophotometric method. In performing the latter method, generally used for the subject purpose, alantion and hydrogen peroxide are first obtained by oxidizing uric acid by uricase. Then, the obtained hydrogen peroxide is mixed with peroxidase and a color rendering reducing agent, such as o-dianisidine and 4-aminoantipyrine.phenol, for color rendering. Further, a suitable wavelength is selected to determine concentration of the uric acid. This method is susceptible to interferences caused by interference sources in human body, such as vitamin C, bilirubin and solved blood, and thus an error is unavoidably introduced. In addition, these conventional analyses also have the disadvantages of long detection time and troublesome operating steps. Further, no real time outputted detection data may be obtained by using these methods.

In this regard, various analysis technologies have been set forth by looking at these disadvantages, in which electrochemical principle is relied on.

In 1974, an uric acid biosensor was first set forth in an article by M. Nanjo and G. G. Guilbaut, entitled "Properties of carbon fiber micro-electrode as a basis for enzyme biosensor", Anal. Chem., Acta. 46, vol. 12, 1974, pp. 275-283. In this technology, biosensing of concentration of uric acid is conducted based on determination of a consumed amount of oxygen by fixing bovine serum albumin (BSA) on oxygen-contained electrodes with glutaraldehyde, with a linear range of up to 0.5 mM. However, since dissolubility of oxygen may vary as temperature and ambient environment vary, this method has the disadvantage of being limited by the maximum oxygen dissolubility, which is 8 ppm or $2.5 \times 10^{-4}$ M under a pressure of 1 atm and a temperature of 25° C.

In 1991, a method for determining concentration of uric acid was proposed in an article by T. Tatsuma and T. Watanable, entitled "Oxidase/peroxidase bilayer-modified electrodes as sensor for lactate, pyruvate, cholesterol and uric acid", Anal Chim Acta, 1992, vol. 242, pp. 85-89. In this method, peroxidase is first fixed on a tin (VI) oxide electrode with glutaraldehyde through a covalent bonding mechanism and then uricase and ferrocenemonocarboxylic acid are added into a working buffer solution. As such, concentration of the uric acid may be determined in a low temperature without being interfered by vitamin C, with a linear arrange of up to 7.5 μM-1 mM achieved.

In 1992, a method for indirectly determining concentration of uric acid was proposed in an article by M. Shaolin, K. Jinqing and Z. Jianbing, entitled "Bioelectrochemical response of the polyaniline uricase electrode", Electroanal Chem, 1994, vol. 334, pp. 121-132. In this method, uricase is firmly buried within a polyanline film since such polyanline film is provided with a good stability and conductivity so that the negative-charged uricase may be successfully enclosed by the polyanline film and hard to run off therefrom. By determining peroxide hydrogen produced by uricase and uric acid, concentration of uric acid may be indirectly determined with a linear range of approximately up to 1.2 μM-1.2 mM. However, the polyanline may have a reduced conductivity as increase of pH value of the ambient environment and cannot exclude other negative-charged substance, delimiting its practical use.

In 1994, another method for indirectly determining concentration of uric acid was set forth in an article by M. T. Gilmartin and J. P. Hart, entitled "Determining with chemically and biologically modified carbon electrodes: a review", Analyst, vol. 120, 1995, pp. 1029-1045. In this method, acetic acid cellulose is first adorned on a stencil print electrode containing ferrocenemonocarboxylic acid and uricase is then fixed on the electrode. By determining peroxide hydrogen produced by reaction between uricase and uric acid, concentration of uric acid may be determined in an indirect manner. This working electrode having a multi-layered structure forms a shield and thus interferences may not be involved with the determination process.

In 1995, another method for determining concentration of uric acid is proposed in an article by O. Eleke, D. Moscone, K. Venema and J. Korf, entitled "Bi-enzyme reactor for electrochemical detection of low concentration of uric acid and glucose", Clin Chim Acta, vol. 239, 1995, pp. 153-165. In this method, uric acid is clinically analyzed by using flow injection analysis (FIA) method. In determining concentration of the uric acid, uricase and horseradish peroxidase are fixed on a nitric acid cellulose film in a physically adsorptive manner. Further, ferrocenemonocarboxylic is also added. As such, concentration of uric acid may be determined in the presence of a low voltage through which the determination process may be prevented from interferences, with a linear arrange approximately up to 30 nM-200 µM.

In 1996, an article by E. Miland, A. J. Miranda Ordieres, P. Tunon Blanco and M. R. Smyth, entitled "Poly(o-aminophenol)-modified bienzyme carbon paste electrode for the detection of uric acid, Talanta, vol. 43, 1996, pp. 785-796. Uric acid and peroxidase bi-enzymes are mixed into a carbon paste electrode and then a single o-amino-phenol layer is electropolymerized on the electrode so that interferences may be removed. However, a huge amount of enzyme has to be involved in manufacture of the working electrode, increasing cost thereof and thus making unsuitable for hitting the market. In this technology, a linear range of 3 µM-10 mM is achieved. In the same year, another uric acid sensor is set forth in an article by Z. Gong and Z. Zhang, "A fiber optic biosensor for uric acid based on immobilized enzymes", Anal. Lett, vol. 5, 1996, pp. 695-709. In the article, concentration of uric acid is determined by a fiber optic biosensor, in which uricase, peroxidase and bovine serum albumin (BSA) are fixed on an optic fiber. First, uric acid is oxidized by uricase and hydrogen peroxide is thus produced. Then, hydrogen peroxide is catalyzed by horseradish peroxidase, turning fluorescence Thiamine into Thiochrome. By determination of intensity of fluorescence emitted from Thiochrome, concentration of uric acid may be determined, with a linear range of 3 µM-30 µM.

In 1998, another method of determining concentration of uric acid is set forth by Susumu Kuwabata, Takahiro Nakaminami, Shin-ichiro Ito and Hiroshi Yoneyama, entitled "Preparation and properties of amperometric uric acid sensors", Sensors and Actuator B, vol. 52, 1998, pp. 72-77. In this method, a self-assembled monolayer is adorned on an Au electrode and the uricase is fixed on the electrode. Further, potassium hexacyanoferrate (III) is added into a working buffer solution so as to avoid from interferences with the determination of concentration of uric acid. Then, an electrochemical method is used to determine concentration of uric acid, by which a linear range of about 0.1 mM-0.6 mM is achieved.

In 1999, another method for determining concentration of uric acid is set forth by Takahiro Nakaminami, Shinichiro Ito, Susumu Kuwabata and Hiroshi Yoneyama, "A biomimetic phospholipid/alkanethiolate bilayer immobilizing uricase and an electrode for amperometric determination of uric acid", Analytica Chemistry, vol. 71, 1999, pp. 4278-4283. In this method, a self-assembled monolayer is adorned on an Au electrode and uricase and 1-methoxy-5-mehylphenazinium are fixed on the electrode in a bi-layer configuration. Then, an electrochemical method is used to determine concentration of uric acid, by which a linear range of about 0.1 mM-0.8 mM is achieved.

In 2000, another method for determining concentration of uric acid is set forth by Shi-ting, Wen, Development and application of current-determination based uric acid biosensor, Biotechnology Institute, Chinese Culture University, Thesis for Master's degree, 2000, pp. 1-89. In this method, a carbon electrode is used as a working electrode and uricase and horseradish peroxidase are fixed on the electrode. Further, ferrocenemonocarboxylic acid is also added into a working buffer solution. By means of an electrochemical method, concentration of uric acid is determined with a linear range of 0.01-2 mg/dl.

Patent wise, the following has been disclosed.

Yen-Shih Shen et al. disclosed a disposable non-enzymatic uric acid determining electrode specimen in U.S. Pat. No. 6,258,230 "Non-enzymatic disposable uric acid detecting electrode strip, method for manufacturing the same and application therefor". With an external voltage of below 400 mV and a pH value set between 7 and 10, concentration of uric acid in solution may be directly determined. In case of concentration of uric acid in human body by the electrode specimen, interferences from other components and vitamin C in blood may be avoided. In determination of concentration of uric acid, serum or blood may be directly used for the electrode specimen. Such kind of electrode specimen is mainly manufactured by ferrocenemonocarboxylic acid dissolvable in water and easy to be carried and mass-produced.

Yen-Shih Shen et al. disclosed a disposable non-enzyme uric acid determining electrode specimen in R.O.C. Patent 00369411 "Disposable current-determination based non-enzymatic uric acid electrode specimen and manufacturing method and application therefor". With an external voltage of below 400 mV and a pH value set between 7 and 10, concentration of uric acid in solution may be directly determined. In case of concentration of uric acid in human body by the electrode specimen, interferences from other components and vitamin C in blood may be avoided. In determination of concentration of uric acid, serum or blood may be directly used for the electrode specimen. Such kind of electrode specimen is mainly manufactured by ferrocenemonocarboxylic acid dissolvable in water and easy to be carry and mass produced. In this patent, a diagnosis and reagent system is disclosed, in which alkaline tungsten phosphate and body fluid without protein contained react with each other and thus a sulfur-containing composite is produced. As such, concentration of uric acid may be determined.

In U.S. Pat. No. 4,348,208, Robert L. Long disclosed a diagnostic assay and reagent system for the determination of uric acid directly on a non-deproteinized sample of a biological fluid using an alkaline phosphotungstate reduction reaction in the presence of at least one organic sulfhydryl-containing compound.

Douglas E. Faulkner disclosed an uric acid detecting mode in U.S. Pat. No. 4,234,313 "Device and method for quantitative uric acid testing". A color indicator disposed on a substrate is used to display a specific color based on the principle that color of uric acid disappear after combination with a reagent. As such, concentration of uric acid may be directly determined. In this detecting mode, a thin film is involved to prevent from deposition of other interference sources.

E. Melvin Gindler disclosed an aqueous solution useful in connection with a redox type spectrophotometric or calorimetric determination of uric acid in a biologic fluid in U.S. Pat. No. 4,072,627 "Uric acid determination". The solution contains either a multivalent metallic ion reducible to a lower valence state by uric acid, a water soluble chelating compound capable of complex with a metallic ion after reduction by uric acid to yield, in complexes form, a colored complex, or a combination of said ion and said chelating compound. The solution also contains, as an added constituent, imidazole, an alpha-amino acid, or a combination thereof. This constituent is present in an amount such that, when said solution contains a biologic fluid containing protein and uric acid, a buffer system such that the pH of the solution is 6 to 12, and a multivalent metal ion, the protein in the fluid does not significantly reduce said multivalent ions present in the solution.

In U.S. Pat. No. 6,699,720, Tsai-Yun Lee et al. disclosed an interference-eliminating membrane for use in detecting uric acid in a sample. The patent related to the interference-eliminating membrane for use in detecting uric acid in a sample, comprising a compound for inhibiting or shading uric acid interfering substances, or derivatives thereof, and a carrier having an absorption property and permeability for the sample; and a process for preparing the interference-eliminating membrane. The present invention also provides a test strip for use in detecting uric acid in a sample, comprising a reagent reaction layer or optional interference-eliminating membranes and/or support layers, and a kit comprising the test strip of the invention.

In U.S. Pat. No. 4,379,780, Gunther Gorka and Klaus Stinshoff disclosed a method for determining the concentration of uric acid in a biological material by contacting the biological material with a reagent comprised of uricase, catalase, aldehyde dehydrogenase, a lower alkanol, and nicotinamide adenine dinucleotide or nicotinamide adenine dinucleotied phosphate, the improvement which comprises determining the uric acid content in the presence of 2-mercaptosuccinic acid.

In U.S. Pat. No. 4,317,878, Toru Nakanishi and Yoshimi Shigemasa disclosed a method for quantitative determination of uric acid in sample by using acidic uricase that is produced by fermentation of a microorganism of the genus Streptomyces.

In light of the above, there are still some shortcomings inherent in the prior art and thus improvements therefor are in an urgent need. In this regard, the Inventors have paid many efforts in the related research and finally developed successfully a amperometric sensor for uric acid and a manufacturing method therefor in the present invention.

SUMMARY OF THE INVENTION

The present invention provides an amperometric sensor for uric acid and a manufacturing method therefor, in which a carbon electrode is provided and oxidation and reduction potentials are determined. Since the carbon electrode is low in cost, easy to be packaged and suitable for mass production, making the thus-formed sensor to be a good choice of a disposable sensor.

Furthermore, the present invention provides an amperometric sensor for uric acid and a manufacturing method for such sensor, in which a carbon electrode is used. Such sensor has the advantages of superior sensibility, sensing range, easy manufacturing process and low cost, compared with the prior art.

The present invention also provides an amperometric sensor for uric acid which may be taken as a biosensor of any kind and a manufacturing method therefor, in which a carbon electrode is manufactured by a stencil print method, reducing cost of such sensor and thus making such sensor disposable.

In the amperometric sensor for uric acid and the manufacturing method therefor, a high polymer formed by a mixture of polyacrylamide, uricase and ferrocenecarboxylic acid is fixed on the carbon electrode. Such carbon electrode may be miniaturized and has a high response speed and good electric characteristics. Further, such carbon electrode may real time monitor and determine characteristics of a subject solution.

DETAILED DESCRIPTION OF THE INVENTION

Figure 1:
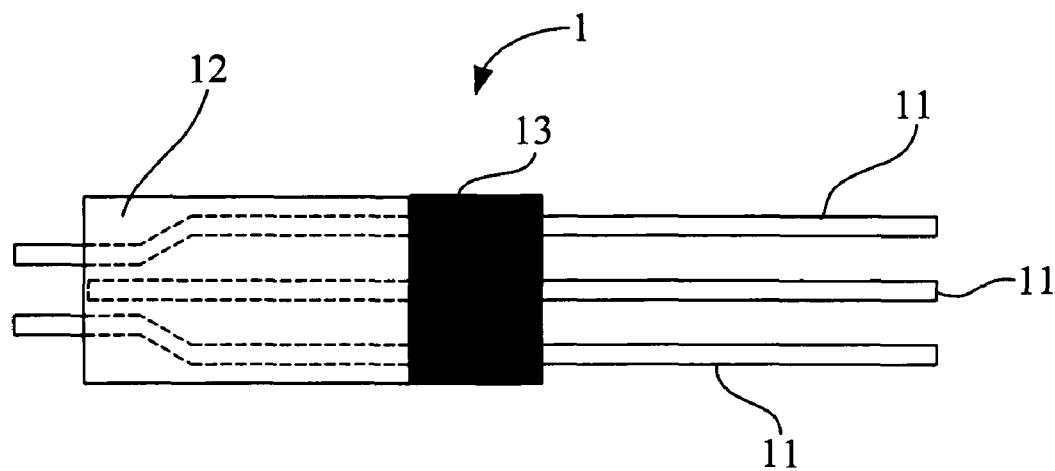
FIG. 1 shows the structure of a carbon electrode of the uric acid sensor of the present invention.

The amperometric sensor for uric acid of the present invention is manufactured through the following steps.
- (a) Fixing a conducting wire 11 on a carbon electrode 12 with a silver paste and then baking the carbon electrode 12 in an oven at a temperature of 100 to 150° C. for about 60 minutes.
- (b) Packaging the portion of the sensor device containing the conducting wire 11 with epoxy 13 and then baking the sensor device in an oven at a temperature of 100 to 150° C. for 60 minutes. As such, a tri-polar carbon electrode 1 is completed for manufacturing, and a structure of which is shown in FIG. 1.
- (c) Forming the tri-polar carbon electrode 1 in an area of 0.1 to 0.5 $cm^2$ with a sensing window thereon.
- (d) Mixing polyacrylamide and a phosphate solution at a ratio of 1:2 (v/v).
- (e) Forming a polyacrylamide solution by mixing the polyacrylamide used in (d) with ferrocenecarboxylic acid at a ratio of 95:5 (w/v).
- (f) Diluting uricase with the polyacrylamide solution obtained in (e) to the activity concentration of 0.6 U/μl.
- (g) Dripping 1-10 ul of the diluted uricase obtained in (f) on the sensing window, and distributing the diluted uricase uniformly thereon, and then air-drying the diluted uricase to fix it, and the amperometric sensor for uric acid is achieved.

The conducting wire used in the invention is made by aluminum.

Figure 2:
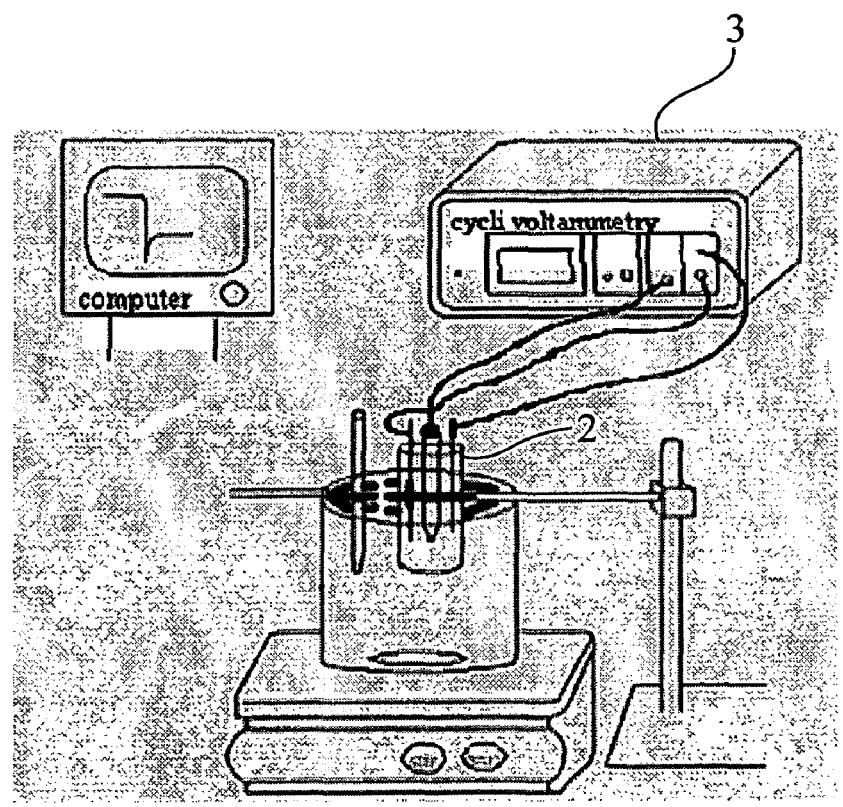
FIG. 2 shows the structure of the uric acid sensor of the present invention.

Referring to FIG. 2, a structure of detection of the amperometric sensor for uric acid is shown therein. The measurement of structure based on the formation of hydrogen peroxide during the enzyme-catalyzed reaction. The hydrogen peroxide is detected by the amperometric method during oxidation at the enzyme electrode. As shown, in the sensor 2 capable of determining concentration of uric acid in a subject solution, oxidation and reduction potentials of an enzyme electrode are detected by a cyclic voltammetry 3. Then, a current signal and a calibration curve of the subject solution may be used to determine sensibility of the enzyme electrode. The detecting method of the current is a enzyme electrode and included the following steps:
- (a) Using a cyclic voltammetry as a readout circuit.
- (b) Contacting a sensing membrane of the uricase electrode with the buffer solution.

(c) Drafting a calibration curve of the current to uric acid concentration to be the response plot of amperometric.

Figure 3:
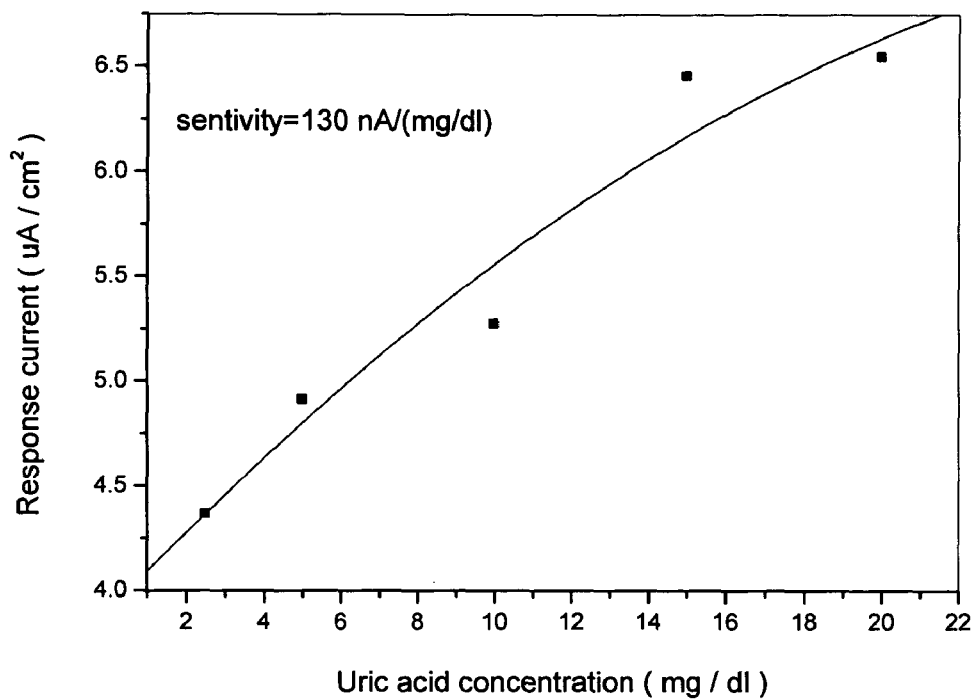
FIG. 3 shows a calibration curve of the uric acid sensor in 10 mM phosphate buffer solution with sodium chloride.

FIG. 3 shows the calibration curves of the uric acid sensor in 10 mM phosphate buffer solution with sodium chloride. It measures current of different uric acid concentrations by cyclic voltammetry. According to the diagram, the linear regression curve of the uric acid concentration that is between 2.5 mg/dl and 20 mg/dl and the sensitivity is 0.13 uA/cm$^{-2}$ (mg/dl)$^{-1}$.

Figure 4:
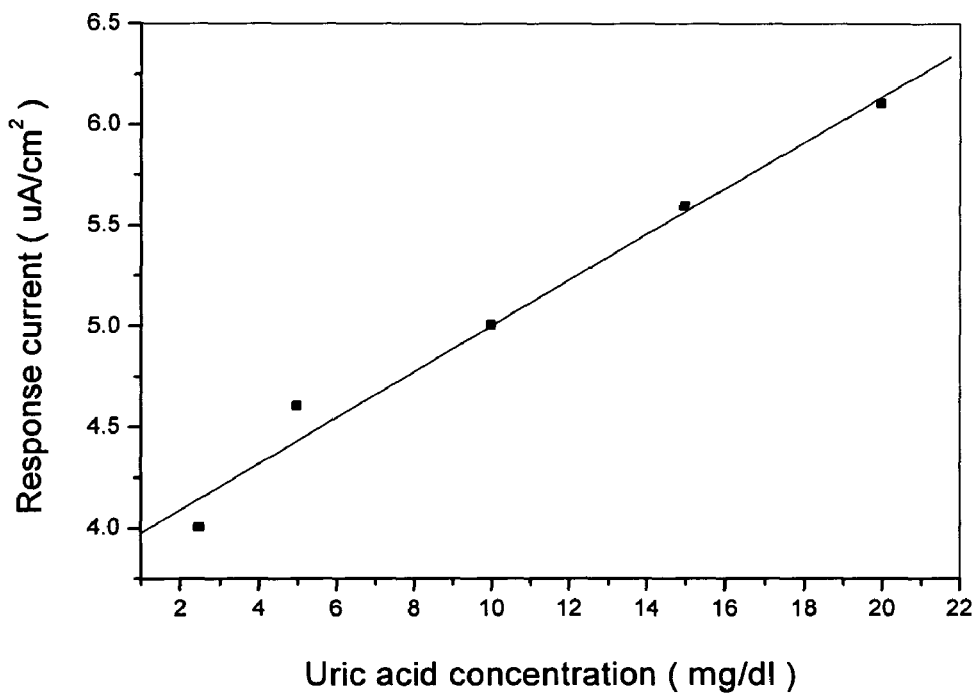
FIG. 4 shows a calibration curve of the uric acid sensor without catalase in 10 mM phosphate buffer solution with sodium chloride.

FIG. 4 shows a calibration curve of the uric acid sensor without catalase in 10 mM phosphate buffer solution with sodium chloride. It measures current of different uric acid concentrations by cyclic voltammetry. According to the diagram, the active site of enzyme is easy to combine with uric acid and hydrogen peroxide are detected by the amperometric method during oxidation at enzyme electrode.

Figure 5:
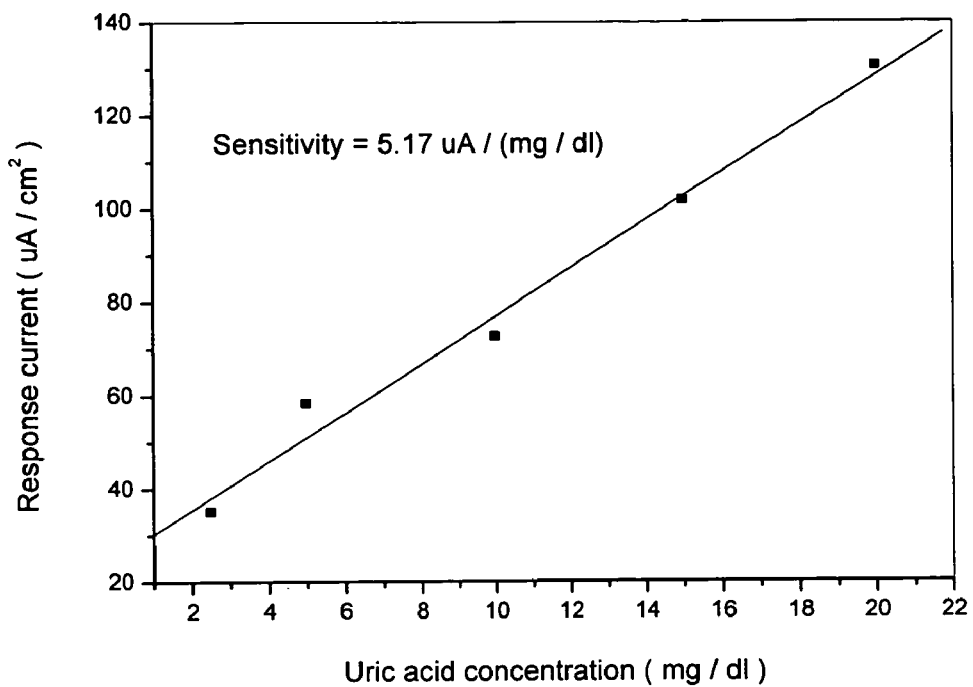
FIG. 5 shows a calibration curve of the uric acid sensor in 10 mM phosphate buffer solution without sodium chloride.

FIG. 5 shows a calibration curve of the uric acid sensor without catalase in 10 mM phosphate buffer solution without sodium chloride. It measures current of different uric acid concentrations by cyclic voltammetry. According to the diagram, the linear regression curve of the uric acid concentration that is between 2.5 mg/dl and 20 mg/dl and sensitivity is 5.17 uA/cm$^{-2}$ (mg/dl)$^{-}$.

Figure 6:
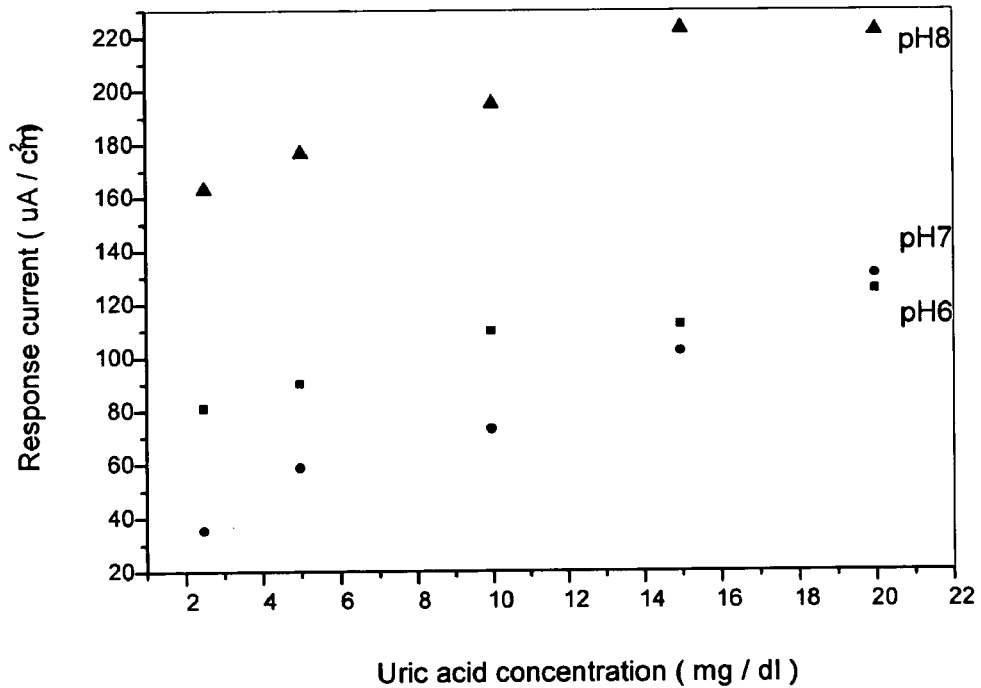
FIG. 6 shows a calibration curve of the uric acid sensor in 10 mM phosphate buffer solution of different pH values.

FIG. 6 shows a calibration curve of the uric acid sensor without catalase in 10 mM phosphate buffer solution of different pH values. It measures current of different uric acid concentrations by cyclic voltammetry. According to the diagram, the linearity is good between 2.5 mg/dl and 20 mg/dl, and the enzyme unit is 1.2 U at 200 mV versus Ag/AgCl. The response time is 65 seconds, the pH range is found to be pH6-pH8 and the sensing area is 0.11 cm$^2$. The response current increases with increasing the enzyme unit. When pH is increased, the response current is increased but linear range is decreased. Therefore the optimum pH will increase the linear range.

Figure 7:
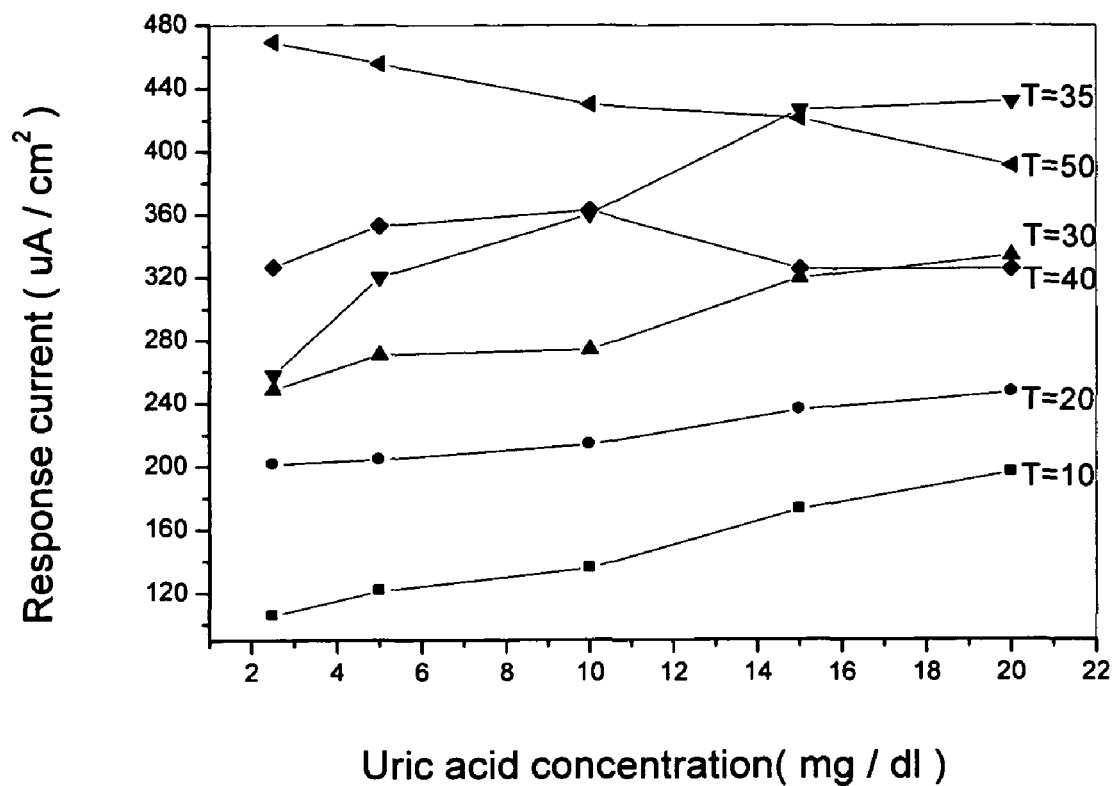
FIG. 7 shows a calibration curve of the uric acid sensor in 10 mM phosphate buffer solution of different temperatures.

FIG. 7 shows a calibration curve of the uric acid sensor without catalase in 10 mM phosphate buffer solution of different temperatures. It measures current of different uric acid concentrations by cyclic voltammetry. According to the diagram, the linearity is good between 2.5 mg/dl and 20 mg/dl, and the enzyme unit is 1.2 U at 200 mV versus Ag/AgCl. The response time is 65 seconds, the optimum pH is found to be pH7.1, the temperature range is 10-30° C. and the sensing area is 0.11 cm$^2$. The oxygen is necessary in this enzyme-catalyzed reaction. When temperature is increased, the amount of oxygen is decreased, and the current is increased. Therefore, the linear range doesn't increase with increasing the temperature.

In conclusion, the amperometric sensor for uric acid and the manufacturing method therefor provide reliability and completeness and further provide the following advantages as compared to the prior art.

1. Polyacrylamide is used to bury uricase and ferrocenecarboxylic acid therein. Such fixation manner may be achieved at a low cost and by a simple manufacturing process.
2. The ratio of uricase and ferrocenecarboxylic acid provided in the invention may lead to an improved sensibility and sensing range.
3. The detection device may not only be used to determine sensing characteristics of the inventive current-determination uric acid sensor but also sensing characteristics of other current-determination uric acid sensors.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims and their equivalents.

What is claimed is:

1. A manufacturing method for an amperometric sensor for uric acid, comprising the steps of:
   (a) fixing a conducting wire on a carbon electrode with a silver paste and then baking the carbon electrode in an oven, said conducting wire comprising aluminum;
   (b) packaging the portion of the sensor device containing the conducting wire with epoxy and then baking the sensor in an oven to manufacture a tri-polar carbon electrode;
   (c) forming the tri-polar carbon electrode having a sensing window thereon;
   (d) mixing polyacrylamide and a phosphate solution;
   (e) forming a polyacrylamide solution by mixing the polyacrylamide used in step (d) with ferrocenecarboxylic acid;
   (f) diluting uricase with the polyacrylamide solution obtained in step (e); and
   (g) dripping a proper amount of the diluted uricase obtained in step (f) on the sensing window, and distributing the diluted uricase uniformly thereon, and then air-drying the diluted uricase to fix it, and the amperometric sensor for uric acid is achieved.

2. The manufacturing method for an amperometric sensor for uric acid according to claim 1, wherein in the step (a) the carbon electrode having the silver paste is placed in the oven for 60 minutes at a temperature of 100 to 150° C.

3. The manufacturing method for an amperometric sensor for uric acid according to claim 1, wherein in the step (b) the carbon electrode having the silver paste is placed in the oven for 60 minutes at a temperature of 100 to 150° C.

4. The manufacturing method for an amperometric sensor for uric acid according to claim 1, wherein the tri-polar carbon electrode has a working electrode area of 0.1-0.5 cm$_2$.

5. The manufacturing method for an amperometric sensor for uric acid according to claim 1, wherein in the step (d) the polyacrylamide and the phosphate solution are mixed at a volume to volume ratio of about 1:2.

6. The manufacturing method for an amperometric sensor for uric acid according to claim 1, wherein in the step (e) the polyacrylamide and the ferrocenecarboxylic acid are mixed at a weight to volume ratio of about 95:5.

7. The manufacturing method for an amperometric sensor for uric acid according to claim 1, wherein in the step (g) the proper amount of diluted uricase is about 1 to 10 ul.

8. The manufacturing method for an amperometric sensor for uric acid according to claim 1, wherein in the step (g) the proper amount of diluted uricase is about 2 ul.

* * * * *